(12) United States Patent
Pawliszyn

(10) Patent No.: US 6,481,301 B2
(45) Date of Patent: Nov. 19, 2002

(54) NEEDLE TRAP

(76) Inventor: Janusz B. Pawliszyn, 383 Dunvegan Dr., Waterloo, Ontario (CA), N2K 1W7

( * ) Notice: Subject to any disclaimer, the term of this patent is extended or adjusted under 35 U.S.C. 154(b) by 53 days.

(21) Appl. No.: 09/771,666

(22) Filed: Jan. 30, 2001

(65) Prior Publication Data

US 2001/0032521 A1 Oct. 25, 2001

Related U.S. Application Data

(60) Provisional application No. 60/179,754, filed on Feb. 2, 2000.

(51) Int. Cl.[7] .............................. G01N 1/24; G01N 1/14
(52) U.S. Cl. ................. 73/864.71; 73/864.16; 73/864.21; 73/864.87; 73/864.74; 73/863.23; 422/99; 422/100; 422/101; 604/190
(58) Field of Search .................. 73/864.71, 863.01, 73/864.16, 864.21, 864.87, 863.23; 422/100; 604/126, 190

(56) References Cited

U.S. PATENT DOCUMENTS

| | | | | |
|---|---|---|---|---|
| 4,014,797 A | * | 3/1977 | Raines et al. | 210/446 |
| 4,453,927 A | * | 6/1984 | Sinko | 604/190 |
| 5,064,418 A | * | 11/1991 | Cronin | 604/190 |
| 5,567,619 A | * | 10/1996 | Stone | 436/164 |
| 5,691,206 A | * | 11/1997 | Pawliszyn | 422/58 |

* cited by examiner

Primary Examiner—Hezron Williams
Assistant Examiner—David A. Rogers
(74) Attorney, Agent, or Firm—Daryl W. Schnurr

(57) ABSTRACT

A hand-held syringe-like device has needle containing a trap with a barrel and plunger to draw air into and out of the needle through the trap. In a method of operating the device, particulate matter in air is retained in the trap and subsequently analytes from the trap are desorbed in an analytical instrument.

9 Claims, 10 Drawing Sheets

Scan #

NEEDLE TRAP

This application claims the benefit of No. 60/179,754, filed Feb. 2, 2000.

BACKGROUND OF THE INVENTION

1. Field of the Invention

This Invention relates to an extraction trap device and method of operation thereof and more particularly to a syringe-like device having a needle with a trap located in the needle whereby particulate matter can be collected and directly desorbed into an analytical instrument.

2. Description of the Prior Art

The environmental impact, chemical composition, concentration trends, and health effects of airborne particulate matter have been extensively studied and described in the literature. Current sampling methods involve the use of gravimetric filters or impactor devices, and a wide variety of light and laser scattering devices. Many of the analytical methods for determination of chemical composition of airborne particulate matter require either sophisticated equipment and/or use strict sample preparation techniques. The task of sampling and analysis of airborne particulate matter is often complicated by the complexity of particle size, particle interactions, chemical partitioning between gaseous and particulate phase, and interactions with the sampling media. The health effects of inhaled particulate matter are associated with both the size and shape, as well as chemical toxicity. One of the better known groups of analytes from the latter category are polycyclic aromatic hydrocarbons.

Polycyclic aromatic hydrocarbons (PAH's) have received increased attention in recent years due to their suspected carcinogenic and/or mutagenic nature. Polycyclic aromatic hydrocarbons originate in incomplete combustion, and are commonly found in gasoline and diesel motor exhaust, as by-products of open fires, industrial smoke, cigarette and cigar tobacco and smoke, and in charcoal-broiled foods. Other sources include coal tar, coal tar pitch, wood preserving agents and coatings, mineral oils, and asphalt.

Current sampling methods for PAH's involve the use of high-volume pumps, filters and sorbent cartridges, e.g., NIOSH 5506, NIOSH 5515, and EPA TO-13A. These methods require extraction from a filter (or sorbent) with an appropriate solvent, followed by subsequent analysis by high-performance liquid chromatography (HPLC), fluorescence, UV detection, or gas chromatography/mass spectometry (GC/MS). Many of these methods require considerable sampling expertise and sophisticated sampling equipment, long sample collection and sample preparation time, and strict extraction procedures. Thus, there is a growing demand for faster, simpler and cost-effective sampling for analytical methods for airborne PAH's without compromising low detection limits achievable with some of the conventional methods. In addition, these new techniques should be reusable and environmentally friendly.

The great majority of the analytical methods used for determination of steroids present in inhaler-administered drugs for treatment of asthma use radioimmunoassay protocols, HPLC, and GC combined with MS. However, the latter methods require derivatization prior to injection. Similarly, the sampling and analysis of consumer sprays and aerosols is usually conducted with a sophisticated sampler, or a method is specific to a particular analyte. To date, there is no simple and fast method for screening of a wide variety of many consumer products that are delivered in a form of spray or aerosol.

Solid phase microextraction (SPME) provides an attractive alternative over traditional analytical methods by combining sampling, pre-concentration, and direct (and complete) transfer of the extracted analytes into a standard gas chromatograph (GC). To date, SPME has been successfully applied in numerous environmental applications including air sampling and analysis methods for total volatile organic compounds (TVOC's) and formaldehyde. Several researchers demonstrated that SPME may also be applied to analysis of PAH's in water. Only a few researchers indicated that SPME may be applied to air sampling for PAH's. Chai and Pawliszyn (1995) found naphtalene, phenanthrene, antracene, and fluoranthene by direct exposure of an SPME device in the diesel exhaust.

SUMMARY OF THE INVENTION

It is an object of the present invention to provide a device and method of operation thereof whereby sampling can be carried out with a hand held device without the use of chemicals or other components that are ultimately discharged into the environment, pre-concentration and direct and complete transfer of the extracted analytes from the device into an analytical instrument.

A device for sampling and extracting components of interest from air containing particulate matter has a passageway with two ends. One of the ends is a free end and part of the passageway contains a trap for the particulate matter. The trap is located partway between the ends. There are pressure differential means that can cause air to flow through the trap. The pressure differential means are located on the side of the trap opposite to the free end. The passageway is sized to be placed into an injection port of a suitable analytical instrument.

A method of sampling and extracting components of interest from air containing particulate matter uses a device having a passageway with two ends. One of the ends is a free end and there is a trap in the passageway. The device has pressure differential means that can cause air to flow through the trap. The pressure differential means is located on the side of the trap opposite to the free end. The method comprises operating the pressure differential means to draw air into the passageway, subsequently inserting the passageway into an injection port of an analytical instrument, desorbing analytes from the trap into the instrument and analyzing the results obtained from the instrument.

DESCRIPTION OF A PREFERRED EMBODIMENT

Chemicals and Supplies. All SPME fibers and devices, syringes, vials and 16 PAH standards were purchased from Supelco (Oakville, Ont). Quartz wool was from Chrompack (Walnut Creek, Calif.). Membrane filters were purchased from VWR (Mississauga, Ont). Ultrahigh purity helium was from Praxair (Waterloo, Ont). All needles were from Chromatographic Specialties (Brockville, Ont). The AzmacortS inhaler (Rhone-Poulenc Rorer, Fort Washington, Pa.), Aerochamber® (Trudell Medical, London, Ont.), and the Muskol® insect repellent (Schering-Plough, Mississauga, Ont.) were purchased at a local drug store.

Figure 1:
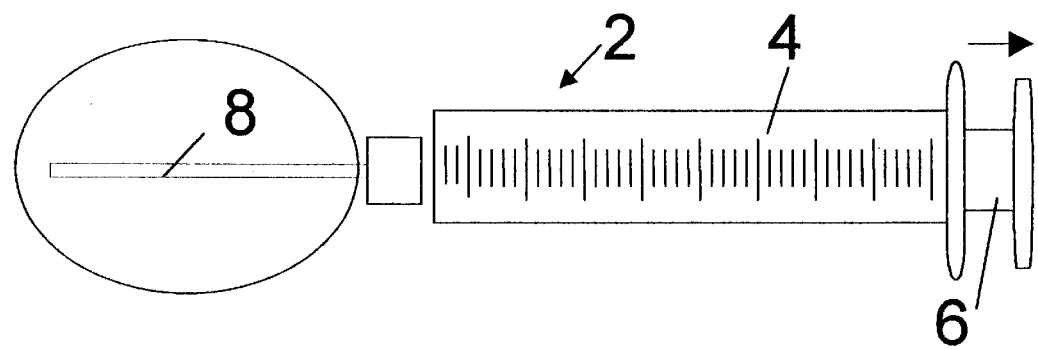
FIG. 1 is a side view of a syringe.
Figure 2:
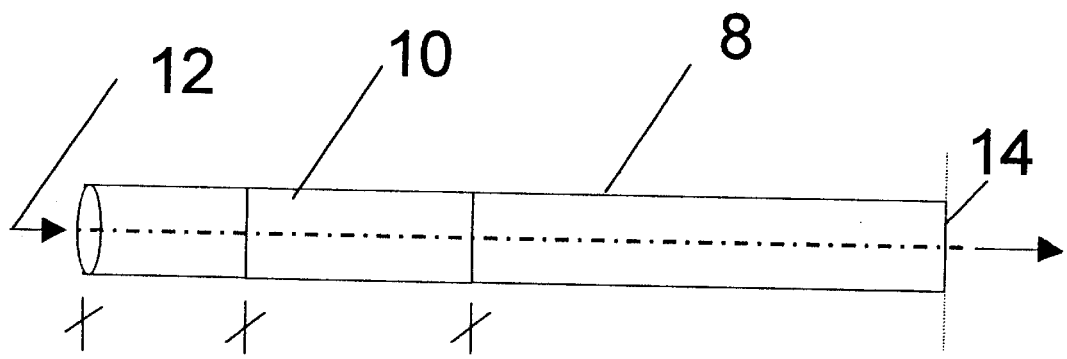
FIG. 2 is an enlarged side view of a needle of the syringe of FIG. 1.

Sampling Devices. A schematic side view of a syringe 2 is shown in FIG. 1. The syringe 2 has a barrel 4 with a plunger 6 and needle 8. The extraction trap device combines the idea of active sampling and solid phase microextraction. FIG. 2 is an enlarged schematic side view of the needle 8 containing a trap 10. The needle 8 has two ends 12, 14 and the end 12 is a free end. The trap 10 is a packing. Air is drawn through the trap 10 by operation of the plunger 6 and the analytes are trapped. However, unlike the conventional methods where some sample preparation step is required to extract the analytes, the device is introduced into a conventional GC injector for sample desorption, similarly to conventional SPME. An additional 10 μL of clean air is delivered immediately after the needle insertion by a gas-tight syringe to aid the introduction of desorption products. The advantages of such a system are many, e.g., the extraction trap device does not require pumps, there are no solvents involved, the total sampling and analysis time is relatively short, and significantly reduced when compared to many existing methods. As such, it can serve as a screening tool, wherever fast analysis is needed. In addition, such a device can also serve as a time-weighted average sampler, where either continuous sampling over long sampling time or a sequence of short sampling events within a required sampling period is used.

Each extraction trap device consists of 40 mm long, gauge 23 stainless-steel needle with a straight, point style #3 opening with quartz wool packing. The quartz wool was packed inside the needle by repeated pushing of the needle opening though a wad of quartz wool that was placed on a clean and flat surface. The position of the packing was determined by placing a stainless steel wire inside the needle at an exact distance from the free end 12 of the needle 8. The packing was then completed by impacting the wool inside with a second wire to the desired depth from the needle opening. For all needles, the 5 mm long packing was positioned 4 mm from the free end 12.

Figure 3:
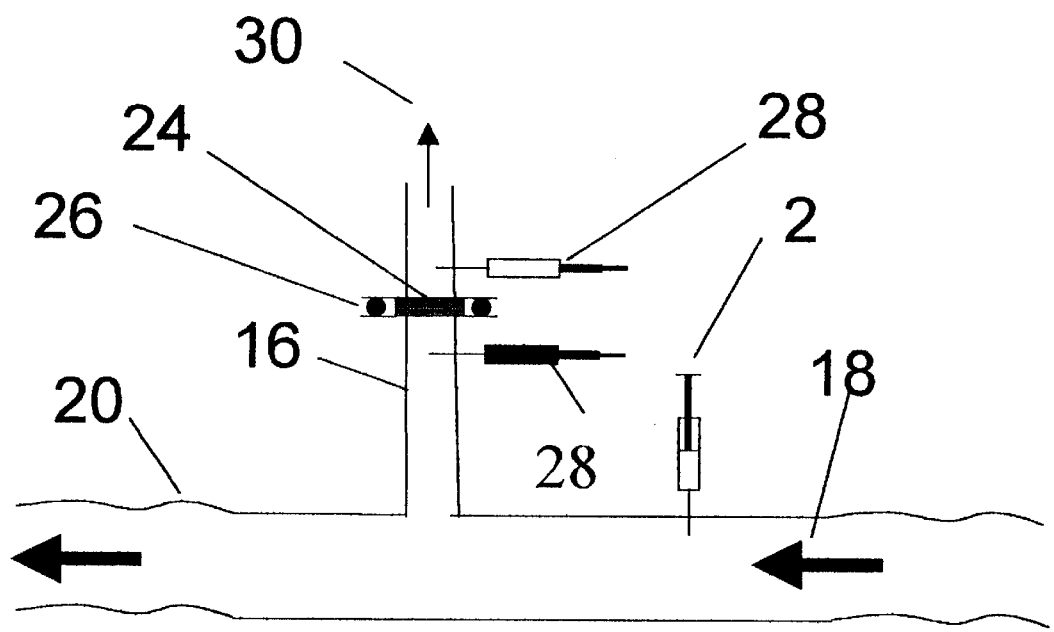
FIG. 3 is a schematic side view of a fluid stream where the stream is tested by the device of the present invention.

For SPME sampling, polydiomethylsilocane (PDMS) 7 μm fibers were used. These fibers are commonly used for analytes with greater partition coefficients, such as all PAH's. In addition, a portable Dusttrak™ model 8520 aerosol monitor (TSI Inc., St. Paul, Minn.) served as both an aerosol sampler and as a pump to provide air flow rate through a membrane filter that was used for particle separation (FIG. 3). This monitor uses a light scattering laser-photometer device, and was used to record particulate matter concentrations with aerodynamic size of 10 μm or lower (PM-10) simultaneously with needle trap and SPME sampling. The Dusttrak™ monitor was factory-calibrated for the respirable fraction of standard ISO 12103-1, A1 test dust, previously known also as the Arizona Test Dust. Although this standard may not be applicable to every type of airborne particulate matter, it may be used as a surrogate measure for common particulates.

Sample Collection. All diesel exhaust samples were collected from a 1998 International 4900 series DT466E truck at the Plant Operations courtyard at the University of Waterloo. Samples were taken when the vehicle was idling (at approximately 750 rpm) using a special sampling train (FIG. 3). Wherever possible, all diesel samples were collected simultaneously with extraction trap devices, SPMF fibers, and the portable aerosol monitor. Diesel exhaust was delivered to and from a 910 mm long stainless-steel pipe 18 (102 mm O.D.) with two 2.4 m sections of corrugated, flexible aluminum tubing 20. Several sampling ports (only one of which is shown) were situated 300 mm from the opening of the pipe. Ports were plugged with half-hole Thermogreen™ septa (Supelco, Oakville, Ont.) to allow insertion of the sampling devices directly into the diesel stream. The septa were wrapped with Teflon™ tape to minimize the sorption. In addition, surface areas of the needle of the extraction trap and SPME needle that were exposed to the exhaust were minimized by using shallow (1 mm) insertion from the septa. This was done to prevent excessive sorption of analytes to non-active parts of samplers, e.g., outside surface of the needles. The alternative technique can be used when no special sampling trains are available. In this case, an SPME fiber (without the holder) is placed inside a modified, 100 mL vial capped with hole cap and Teflon-coated seprum. As a result, only the SPME fiber coating is exposed to an air/exhaust sample and all metal parts of SPME assembly are inside the vial. Such a vial can also serve as a convenient SPME container, for field studies. Sampling was also completed upstream and downstream from a porous 47 mm 0.45 μm filter 24 (VWR, Mississauga, Ont.) that was placed between two Teflon™ rings 26 and flanges inside a 38 mm (1.5 in.) tube 16 FIG. 3). This tube 16 was connected to the main tube 18 and the air sample 30 drawn through the membrane filter using the personal I.H pump (A. P. Buck, Orlando, Fla.) at 1.5 L/min.

Exhaust temperature near the SPME fibers and extraction trap devices was measured using an Omega® K-type thermocouple and Omega® microprocessor thermometer (model HH22) (Omega®, Stanford, Conn.). Sampling was conducted after an initial stabilization period to ensure that during the temperature of the exhaust was constant. The steady-state tenperature at sampling ports varied from 57 to 62° C. for the main tube, and was generally a couple of degrees lower for the membrane area sampling. Exposure times vaied from 1 to 16 min for a single PDMS-7 μm fiber in an SPME device or syringe 2. Air volumes pulled through extraction trap devices 28 were also ranged from 1 and 50 mL to vary the mass load. After sample collection, SPME fibers were pulled approximately 30 mm inside the needle, capped and kept at room temperature before analysis on a Varian Satun-IV GC/MS. Similarly, the extraction trap devices 28 were separated from the sampling syringe, capped and kept at room temperature before analysis. Both devices used a narrow bore Teflon™ plugs for sealing of the needle opening and sample preservation.

Figure 4:
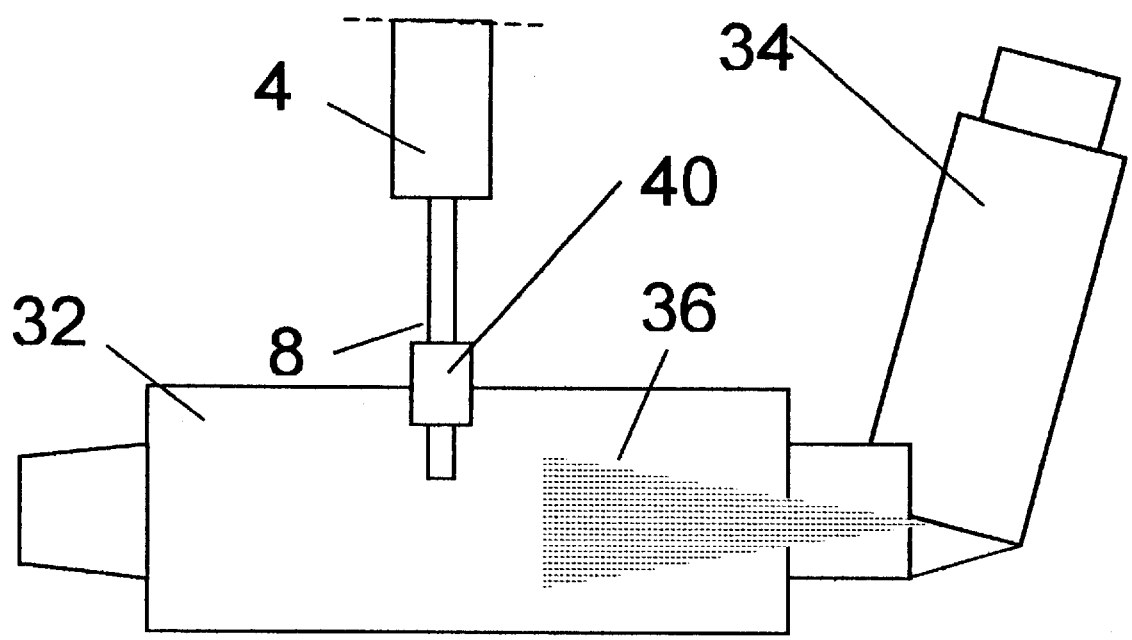
FIG. 4 is a side view of an inhaler where the device of the present invention is used to analyze aerosols.

Aerosol 36 from inhaler-administered Azmacort® 34 was sampled inside an aerosol holding AeroChamber® 32 (FIG. 4). For the purposes of this application, aerosol is considered to be a particulate. Additional sampling ports were made in the middle of the chamber length and plugged with half-hole septa 40 wrapped in Teflon™ tape. The AeroChamber® remained horizontal during all experiments, and at the room temperature. The amount of aerosol 36 was varied by administering 1 to 3 metered doses (puffs). The sampling time for SPME fibers was 10 s. The air volumes varied from 1 to 10 mL for the extraction trap device 28. The device 28 has a syringe 4 and a needle 8 (as shown in more detail in FIGS. 1 and 2). The samples were analyzed for triamcinolone acetonide, the medicinal ingredient used in asthma treatment.

The spray sampling was conducted with both devices inside a 4 L beaker that was used to contain the air during sampling at room temperature. For all experiments, only one short puff of the Muskol® insect repellent was used. Sampling time for the SPME fibers was 10 s, and the volume of air drawn through the extraction trap devices varied form 0.1 to 5 mL. Both spray and the aerosol samples were analyzed on the Varian Satum-IV GC/MS.

Figure 5:
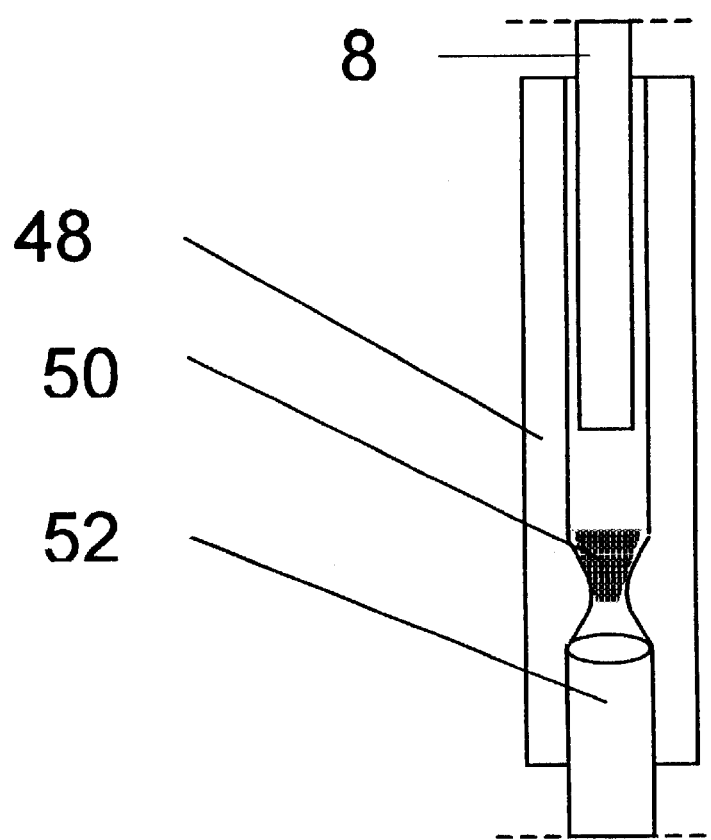
FIG. 5 is a side view of an injection port of an analytical instrument containing the device of the present invention.

Sample Analysis. All samples were analyzed within the next 12 hr following the sample collection. Before and after sample desorption in the GC injector, each fiber was visually inspected under a microscope, to evaluate particulate matter deposition and the effectiveness of particulate removal following 5 min desorption in the GC injector. The conventional injector glass insert (Supelco, Oakville, Ont.) was packed with quartz wool to prevent column loading with unwanted carbonaceous material (FIG. 5). In the case of the extraction trap injections, each needle 8 was first attached to a clean Gastight® syringe (not shown) with a plunger positioned at 10 µL and transferred to a GC injector 48. The analytes were then desorbed from the needle packing and introduced to the carrier gas by a 10 µL air injection. A screen 50 prevents particulate matter from the trap from entering a GC column 52

Analytes were separated on a HP1-MS (60 m×0.25 mm×0.25 µm film) column. The column was held at 50° C. for 0.5 min, ramped at 10° C. /min to 300° C., then held at 300° C. for 14.5 min. Injector and transfer line temperatures were set to 300° C., and 240° C. For liquid injections of the PAH standard, the injector temperature was set to 50° C., followed by ramping with the nominal rate of 300° C./min to 300° C., where it was held for the rest of the run. Ultrahigh purity helium was used as carrier gas at 25 psi. The mass range scanned was from 45 to 285 amu for diesel exhaust, 40 to 440 amu for aerosol, and 40 to 200 amu for the spray analysis, respectively. Sixteen EPA 610 standard (Supelco, Oakville, Ont.) was used for the calibration of PAH the National Institute of Standards and Technology (NIST) spectra library and estimation of column retention times.

Results and Discussion

Figure 8A:
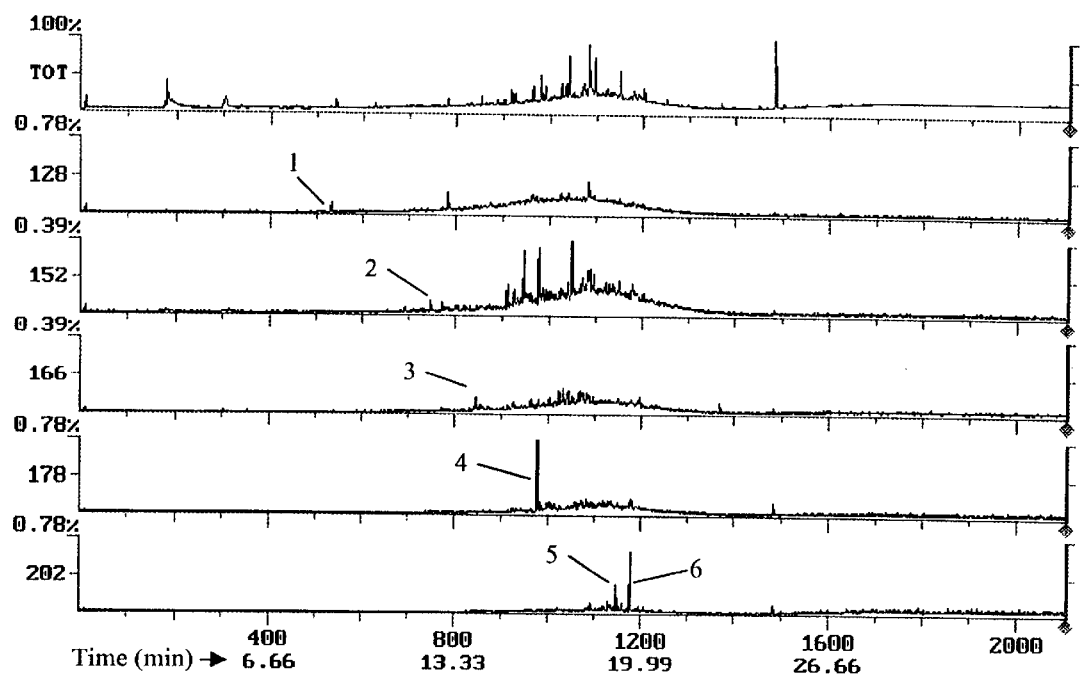
FIG. 8A is a graph of a comparison of typical GC/MS chromatograms for several single ions of diesel exhaust.
Figure 8B:
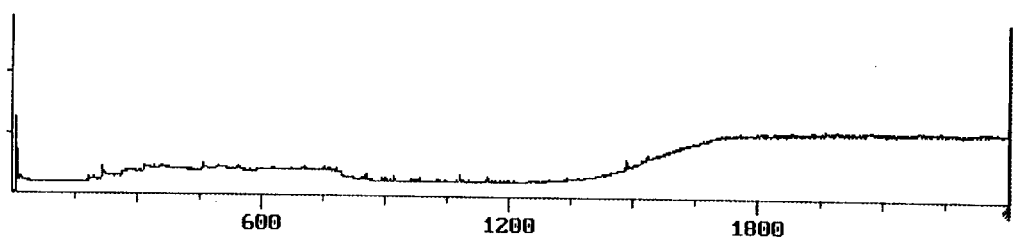
FIG. 8B is a graph of the analytes on the fiber after desorption.

Needle Trap Devices. FIG. 8 shows typical GC/MS chromatograms of a diesel exhaust sampled by the extraction trap of the present invention. FIG. 8 compares samples collected upstream from the filter (from the unfiltered exhaust), (part A), with sample collected downstream from the 0.45 µm cut-off filter (part B). Carry-over from the needle device after 5 min desorption is shown in part B. In the case of (A) and (B), 20 mL of air was drawn through each extraction trap in approximately 2 min. Typically, there was a significant reduction in the GC/MS response to filtered samples. Several target PAH's were identified in both samples, i.e., acenaphtylene, acenaphtene, phenanthrene, fluoranthene, and benzo(ghi)perylene. Only naphthalene and benzo(k)fluoranthene were found in the filtered sample. This finding was consistent with the previous study. In FIG. 8A, 1=naphthalene, 2=accnaphtylene, 3=flourene, 4=phenanthrene, 5-flouranthene and 6=pyrene.

There was no significant carry-over observed, i.e., all PAH's were completely desorbed. Thus, it was determined that extraction trap devices could be routinely reused. Also, no significant deterioration was observed for at least 10 samples. The results presented in FIG. 8 suggest that the extraction trap device could be used as a fast screening tool for analysis of airborne particulates in exhaust samples. Even a relatively low volume sample resulted in significant response on the GC/MS.

Figure 9:
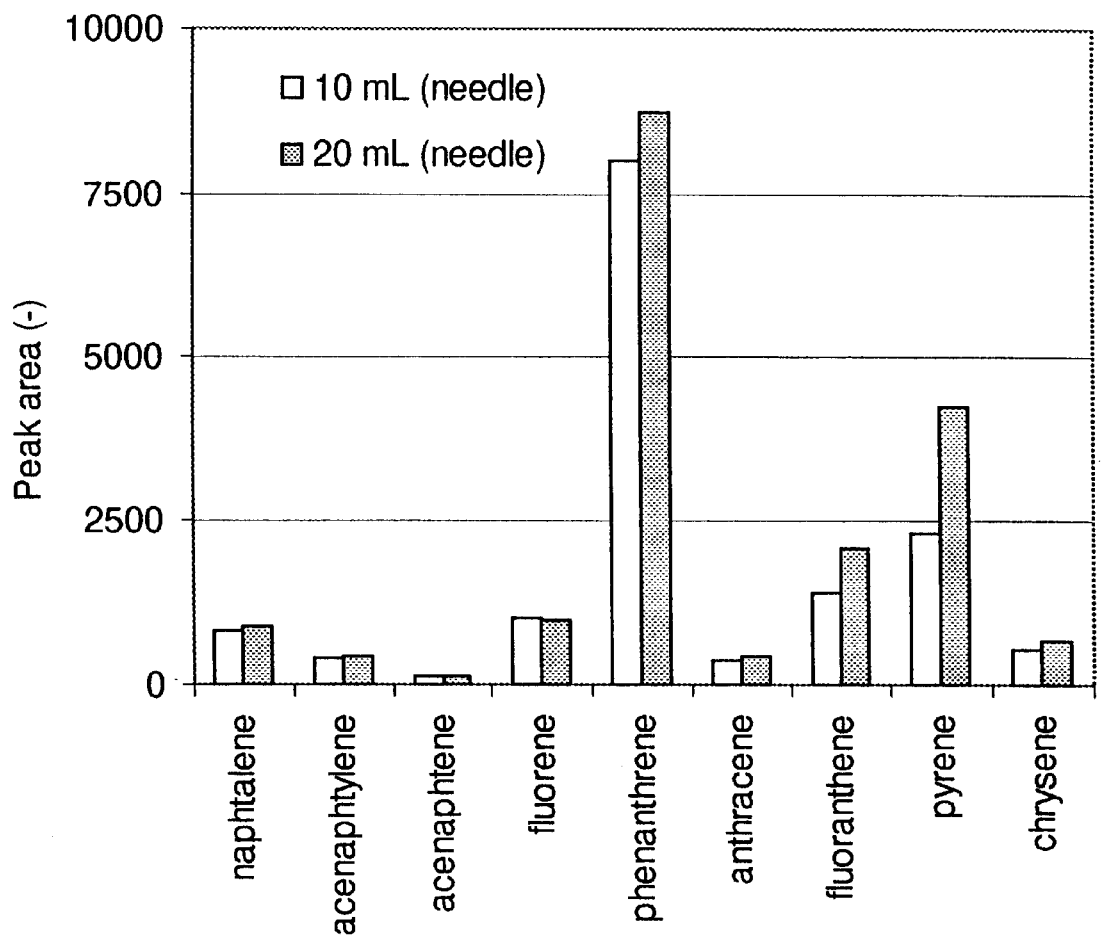
FIG. 9 is a graph showing polycyclic aromatic hydrocarbons extracted from diesel exhaust using the device of the present application

Comparison of PAH extraction from diesel exhaust, collected simultaneously with two extraction trap devices sampling simultaneously 10 and 20 mL of exhaust respectively is presented in FIG. 9. The mass abundance for several target PAH's increased with the air volume that was drawn through each needle. The mass intake did not increase proportionally with the volume likely caused by the fact substantial portion of the PAH's is present in the gas phase, not on the particulate. Initially dissolved PAH's are adsorbing on the surface of the needles until the surface is saturated. This effect is clearly seen for more volatile PAH's, where the uptake does not vary with the sample volume. All else being equal, it can be reasonably expected that the mass of trapped particulate matter in the needle device may be proportional to the air volume, similar to conventional gravimetric filters.

Figure 6A:
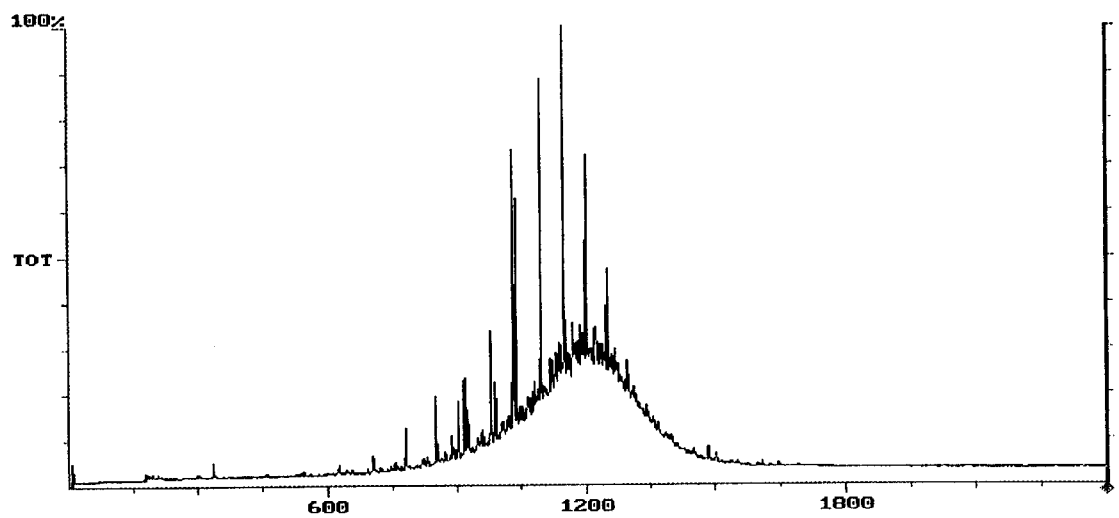
FIG. 6A is a graph of a GC/MS chromatogram of diesel exhaust.
Figure 6B:
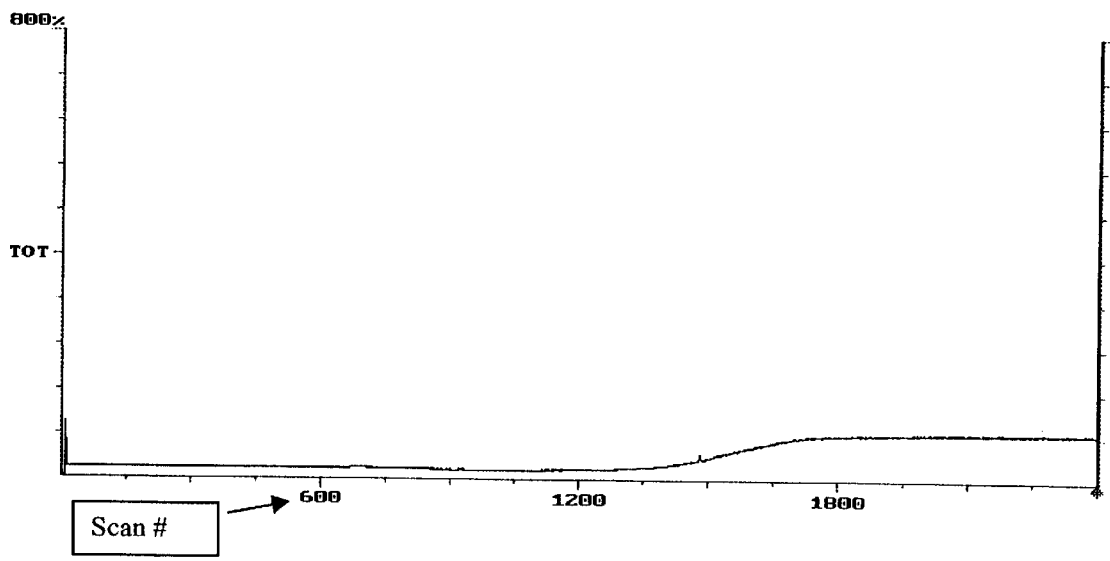
FIG. 6B is a graph of the analytes left on the fibre after desorption.
Figure 7A:
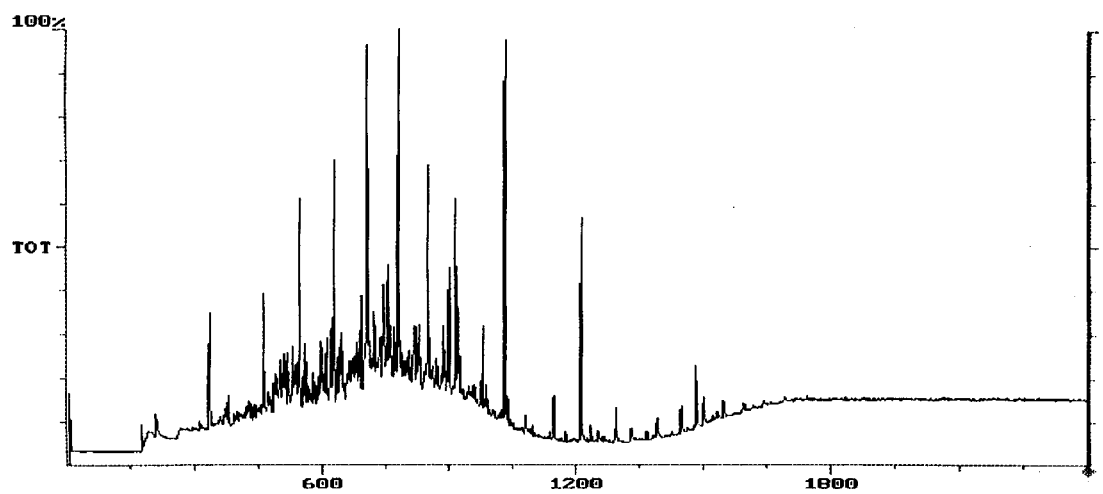
FIG. 7A is a comparison of a GC/MS chromatogram from diesel exhaust collected upstream.
Figure 7B:
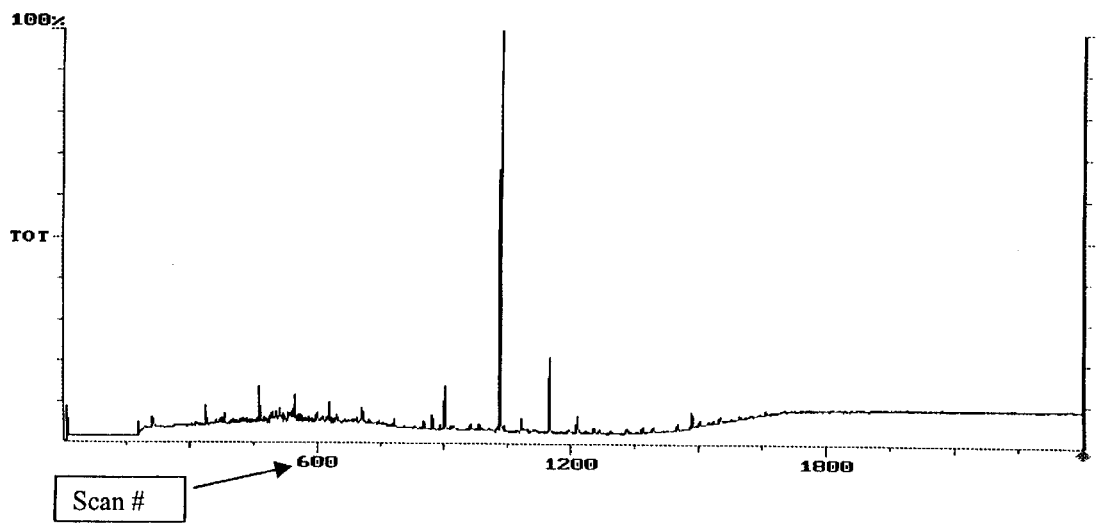
FIG. 7B is a graph of a typical comparison of GC/MS chromatogram from diesel exhaust collected downstream.

SPME Fibers. A typical GC/MS chromatogram of a diesel exhaust sampled by a PDMS 7 µm fiber for 2 min is presented in FIG. 6 (part A). No significant carry-over was observed after 5 min desorption (FIG. 6, part B). Visual inspection with a microscope revealed that particle deposition on the fiber surface was proportional to sampling time. Most of the deposit was removed after 5 minute desorption in the GC/MS injector. Some residual carbonaceous material, however remained on the fiber coating when a long sampling time was permitted. This residue did not appear to have any negative effect on the fiber blank, and the reusability of the fiber. Comparison of chromatographs obtained with the SPME fiber and with the filtered and unfiltered exhaust (FIG. 7) was very similar to chromatograms obtained with the extraction trap device (FIG. 8). Several target PAH's were identified in both samples, i.e., acenaphtylene, phenanthrene, pyrene, benzo(a)anthracene, benzo(k)fluoranthene, benzo(a)pyrene, and benzo(ghi) perylene. A proportional increase of extracted mass with the sampling time was observed for several PAH's. In general, mass abundances (measured as peak areas) for samples collected upstream from the filter were 2 to 10 times greater than those associated with filtered samples. In addition, naphthalene was present only in the upstream sample. The number of PAH's present in the SPME sample collected downstream from the filter was greater than in the same filtered sample collected with the needle device. This result suggests that the SPME fiber was more efficient in extracting the gaseous fraction of PAH's, present in the filtered sample. Furthermore, it is likely that the needle trap device was mechanically trapping larger particles with sorbed PAH's.

Figure 10:
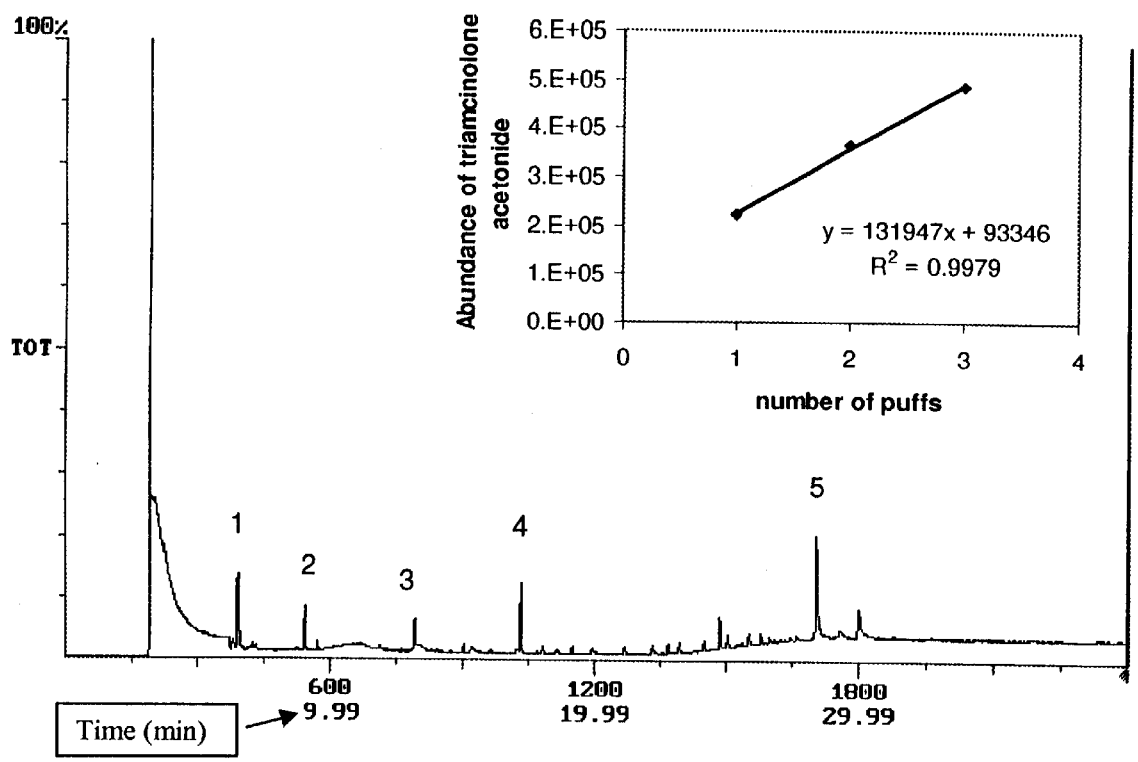
FIG. 10 is a graph of a GC/MS chromatogram of an asthma drug aerosol containing triamcinolone acetonide.

Aerosol Sampling. Example of a chromatogram obtained rising SPME fibers for inhaler-administered Azmacort® are presented in FIG. 10. Triamcinolone acetonide and other peaks were identified using GC/MS NIST library. Both devices were very efficient in collecting significant amounts of steroid, considering that a very short sampling time for SPME (10 s), the relatively small air volume (3 mL) for the extraction trap sample were used. The insert in FIG. 10, presents the increase of the steroid dose with each additional puff. The results presented in FIG. 10, indicate that both sampling devices can be used for fast screening of medicinal aerosols. Such a screening is difficult if not impossible using conventional sampling methods, and gas chromatography/ mass spectrometry.

Figure 11A:
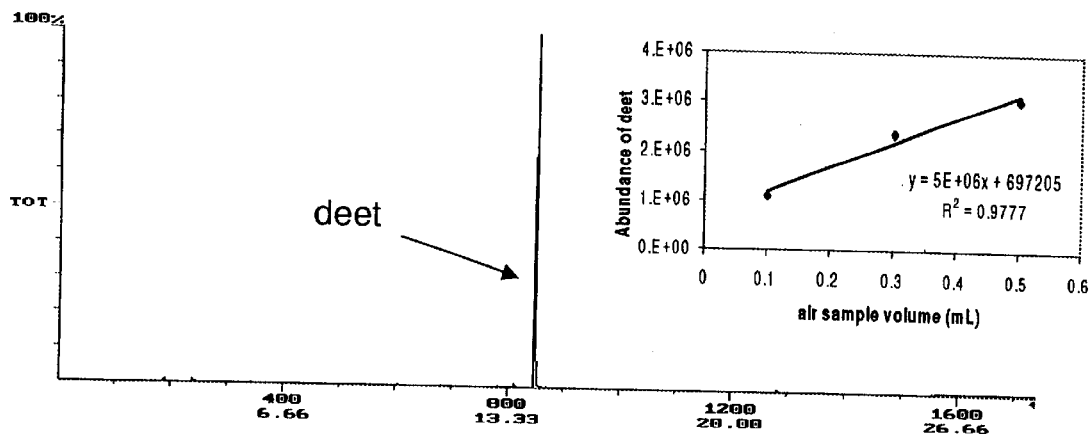
FIG. 11A is a graph of a GC/MS chromatogram of insect repellent using the device of the present invention.
Figure 11B:
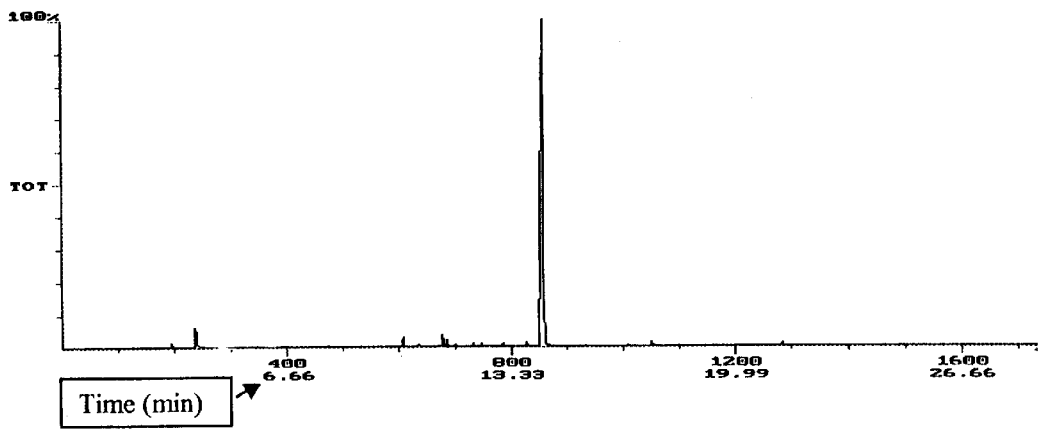
FIG. 11B is a graph of GC/MS chromatograms of insect repellent with a ten second sampling.

Spray Sampling. FIG. 11 presents a comparison of chromatograms obtained from the spray of the insect repellant using the PDMS 7 μm fiber (part A) and the extraction trap device (part B). Deet (n,n-dietbyl-meta-toluamide) and other peaks were identified using GC/MS NIST library. As with the aerosol sampling, both devices were very efficient in extrating significant amounts of deet with a short sampling time for SPME (10 s), and air volume of 1 mL for the extraction trap sample. The insert in FIG. 11 (part A), shows the increase of the deet dose with increasing sample volume.

Development of New Devices. Considering the simplicity, the extraction trap device and SPME fibers provide for sampling of airborne particulate matter, it is possible to envision an extraction sorbent traps, i.e., needles with sorbent packing or coating. Furthermore, combinations of extraction trap devices based on the existing design may be developed in the future. Possible developments may include simultaneous, side-by-side (or parallel) sampling with two needles, sampling with two needles connected in series, or sampling with a single needle containing two-section packing in series. Both devices can also be easily coupled to existing methods for particulate sampling. Possible uses can include determination of partitioning between sorbed and gaseous fraction of PAH's, and other analytes in airborne particulate matter. These devices can be incorporated in conventional, active sampling, upstream and downstream sampling from size separation devices, such as cyclones, nozzles, impactors and porous membranes.

Novel extraction trap devices and SPME fibers were used for sampling of airborne particulate matter. Both devices performed very well when applied to sampling of diesel exhaust, medicinal aerosol, and a consumer product in spray. Both devices proved to very versatile to handle significantly different samples. These devices allowed for simple, inexpensive screening that is very difficult, if not impossible, with conventional methods. Both devices were easy to use and robust in field sampling. It was relatively easy to use each device with little preparation, and sample preservation was generally good. Both devices were reusable, and in the case of needle trap devices, easy to assemble. Further research may be needed to study the effects of aging of needle packing, air velocities in the needle, and the effects of the carbonaceous residue on SPME coatings when fibers are exposed to excessive concentrations of particles. The interesting extension of the work will be investigation of the particle matrices, for example by placing the fiber into appropriate analytical instrument to study its surface or into the plasma to volatilize and determine composition of the matrix.

I claim:

1. A hand held device for sampling and extracting components of interest from fluid containing particulate matter, said device comprising a needle having two ends, one of said ends being a free end, part of said needle containing a trap for said particulate matter, said trap being located part way between ends, pressure differential means that can cause said fluid to flow through said trap, said pressure differential means being located on a side of said trap opposite to said free end, said needle being sized to be placed into an injection port of an analytical instrument where said components of interest on said trap can be desorbed into said instrument.

2. A device as claimed in claim 1 wherein said pressure differential means is removable and replaceable on said needle.

3. A devise as claimed in claim 2 wherein said device is a syringe like device having a barrel, a plunger and said needle, said plunger and barrel being said pressure differential means and connected to said needle so that fluid can be made to flow through said trap by operating said plunger.

4. A device as claimed in claim 3 wherein said trap is quartz wool packing.

5. A device as claimed in claim 3 wherein said trap is located substantially 4 mm from said free end and is substantially 5 mm long.

6. A device as claimed in claim 5 wherein said trap is substantially 5 mm long.

7. A method of sampling and extracting components of interest from fluid containing particulate matter using a device having a needle with two ends, one of said ends being a free end, and a trap in said needle, said device having pressure differential means that can cause fluid to flow through said trap, said pressure differential means being located on a side of said trap opposite to said free end, said method comprising operating the pressure differential means to draw fluid into said needle, subsequently inserting the needle into an injection port of an analytical instrument, desorbing components of interest from the trap into said instrument and analyzing the results obtained from the instrument.

8. A method as claimed in claim 7 wherein said pressure differential means is removable and replaceable and there is a first pressure differential means and a second pressure differential means, said method including the steps of installing said first pressure differential means on said device and operating said first pressure differential means to draw fluid into said needle through said trap to collect a sample, subsequently detaching said first pressure differential means from said needle, installing said second pressure differential means on said needle prior to desorption, inserting said free end of said needle into said injection port of said analytical instrument, operating said second differential pressure means to expel some fluid through said trap while desorbing said components of interest from said trap into said analytical instrument.

9. A method as claimed in claim 7 including the step of using said device in combination with a solid phase microextraction device.

* * * * *